(12) United States Patent
Conney

(10) Patent No.: US 6,358,940 B1
(45) Date of Patent: Mar. 19, 2002

(54) MODIFIED 2-ALKOXYESTRADIOL DERIVATIVES WITH PROLONGED PHARMACOLOGICAL ACTIVITY

(75) Inventor: Allan H. Conney, Princeton, NJ (US)

(73) Assignee: Rutgers, the State University, New Brunswick, NJ (US)

( * ) Notice: Subject to any disclaimer, the term of this patent is extended or adjusted under 35 U.S.C. 154(b) by 0 days.

(21) Appl. No.: 09/644,021

(22) Filed: Aug. 23, 2000

Related U.S. Application Data

(60) Provisional application No. 60/152,781, filed on Sep. 7, 1999.

(51) Int. Cl.[7] .......................... A61P 35/00; A61K 31/56
(52) U.S. Cl. .......................................... 514/182; 552/614
(58) Field of Search ........................... 514/182; 552/614

(56) References Cited

PUBLICATIONS

Cushman et al., Synthesis, antitubulin and antimitotic activity, and cytotoxicity of analogs of 2–methoxyestradiol, 1995, J. Med. Chemistry, 38(12), 2041–9.*

* cited by examiner

*Primary Examiner*—Edward J. Webman
*Assistant Examiner*—Helen Nguyen
(74) *Attorney, Agent, or Firm*—Licata & Tyrrell P.C.

(57) ABSTRACT

Modified 2-alkoxyestradiol compounds wherein all hydrogens of the carbon next to the oxygen of the alkoxy moiety at position 2 are substituted with a halogen, alkyl or aromatic group, or a trifluoromethyl group are provided. Methods of using compositions containing these compounds to inhibit microtubule formation and tubulin polymerization or depolymerization in cells and to treat diseases characterized by abnormal cell mitosis are also provided.

5 Claims, No Drawings

MODIFIED 2-ALKOXYESTRADIOL DERIVATIVES WITH PROLONGED PHARMACOLOGICAL ACTIVITY

INTRODUCTION

This application claims the benefit of provisional U.S. Application Serial No. 60/152,781, filed Sep. 7, 1999.

BACKGROUND OF THE INVENTION

The physiological and pharmacological effects of estradiol, the major ovarian estrogen, are well characterized. In particular, much research has been focused on the involvement of estradiol in endocrine-dependent carcinogenesis. However, less is known about the physiological and pharmacological activities of more than 20 metabolites of estrogen.

2-Methoxyestradiol is a naturally occurring mammalian metabolite formed by hepatic hydroxylation followed by O-demethylation of estradiol (Breuer et al. Naturwissenschaften 1960 12:280–81; Gelbke et al. J. Steroid Biochem. 1976 7:457–463). More research has been focused on this metabolite of estradiol as it has been found to be cytotoxic in cancer cell cultures. The cytotoxicity is associated with uneven chromosome distribution, faulty spindle formation, inhibition of DNA synthesis and mitosis, and an increase in the number of abnormal metaphases (Seegers et al. J. Steroid Biochem. 1989 32:797–809; Lottering et al. Cancer Res. 1992 52:5926–5923).

2-Methoxyestradiol also exerts a strong inhibitory effect on angiogenesis. Administration of 2-methoxyestradiol is thus suggested to be useful in the treatment of pathological angiogenesis and of angiogenic diseases such as angiogenic-sustained solid tumors. See U.S. Pat. No. 5,643,900.

In in vivo studies in mice, 2-methoxyestradiol was found to be a potent inhibitor of neovascularization and to inhibit their growth (Fotsis et al. Nature 1994 368:237–239). No signs of toxicity were observed in these animals.

2-Methoxyestradiol has also been reported to induce apoptosis in cancer cells. Specifically, it was found that 2-methoxyestradiol increases wild-type p53 levels in a human non-small cell lung cancer line associated with accumulation of the cyclin dependent kinase inhibitor p21WAF1/CIP1. See WO 98/042191. Significant apoptotic cell death was observed after drug treatment, thus indicating that 2-methoxyestradiol facilitates induction of p53-mediated apoptosis.

Various analogs of 2-methoxyestradiol have been prepared.

For example, Cushman et al. synthesized an array of 2-methoxyestradiol analogs to define the structural parameters associated with the antitubulin activity and cytotoxicity of this estradiol metabolite (J. Med. Chem. 1995 38(12):2041–2048). 2-Ethoxyestradiol and 2-((E)-1-propenyl)-estradiol were disclosed as being substantially more potent than 2-methoxyestradiol itself. Analogues which inhibited tubulin polymerization also displayed significantly higher cytotoxicity in the MDA-MB-435 breast cancer cell line than in the other cell lines studied. Potencies of these analogues as cytotoxic and mitotoxic agents in cancer cell cultures correlated well with their potencies as inhibitors of tubulin polymerization.

D'Amato et al. (U.S. Pat. No. 5,892,069) discloses a number of estrogenic compounds similar in structure to 2-methoxyestradiol for use as antimitotic agents. Various substitutions of the methoxy at position 2 are disclosed.

In the present invention compositions are provided which comprise a modified 2-alkoxyestradiol structure wherein all of the hydrogens of the carbon next to the oxygen of the alkoxy moiety at position 2 are substituted with a halogen or alkyl group. These modifications in the compositions of the present invention are believed to prevent or inhibit their O-dealkylation thereby extending their pharmacological activity.

SUMMARY OF THE INVENTION

An object of the present invention is to provide a composition comprising a compound of formula (I):

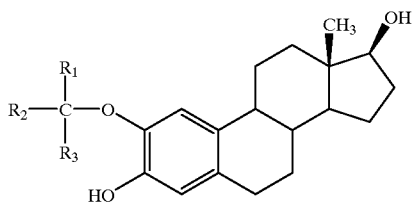

wherein $R_1$, $R_2$ and $R_3$ are each selected from the group consisting of halogens, methyl or longer chain alkyl groups or aromatic groups, and trifluoromethyl groups.

Another object of the present invention is to provide a method of prolonging inhibition of microtubule formation and tubulin polymerization and/or depolymerization via a composition of formula (I).

Another object of the present invention is to provide a method for treating diseases characterized by abnormal cell mitosis via administration of a composition of formula (I). Compositions of the present invention are believed to be particularly useful in treating neoplastic diseases including cancer.

DETAILED DESCRIPTION OF THE INVENTION

Cell mitosis is a multi-step process involving both cell division and cell replication. Mitosis is characterized by intracellular movement and segregation of organelles including mitotic spindles and chromosomes facilitated by polymerization of the cell protein tubulin. Polymerization of α- and β-tubulin results in formation of microtubules which are important for cell mitosis, cell locomotion and movement of specialized cell structures such as cilia and flagella.

Cell mitosis is important in the normal development of the embryo, formation of the corpus luteum, wound healing, inflammatory and immune response, and angiogenesis.

However, abnormal cell mitosis is a characteristic of numerous diseases, the hallmark being cancer and/or neoplastic diseases. Other mammalian diseases characterized by abnormal cell mitosis include, but are not limited to, excessive or abnormal stimulation of endothelial cells such as in atherosclerosis, benign tumors such as hemangiomas, acoustic neuromas, neurofibromas, trachomas, and pyogenic granulomas, vascular malfunctions, abnormal wound healing, inflammatory and immune disorders, Bechet's disease, gout or gouty arthritis, abnormal angiogenesis accompanying rheumatoid arthritis, psoriasis, diabetic retinopathy, and other ocular angiogenic diseases such as retinopathy of prematurity (retrolental fibroplastic), macular degeneration, corneal graft rejection, neovascular glaucoma and Osler Weber syndrome. The present invention relates to compositions for use in treating diseases characterized by abnormal cell mitosis.

Compositions of the present invention are derivatives of 2-methoxyestradiol:

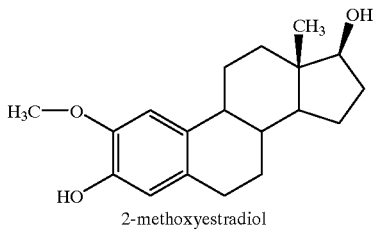
2-methoxyestradiol

Compositions of the present invention comprise formula (I):

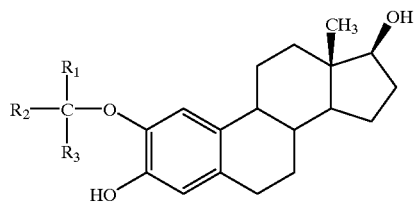

In these compositions, $R_1$, $R_2$, and $R_3$ each comprise a halogen, a methyl or longer chain alkyl group or aromatic group or a trifluoromethyl group. It is believed that the compositions of the present invention will have similar pharmacological activity to 2-methoxyestradiol. Accordingly, it is expected that the compositions of the present invention will inhibit microtubule formation and tubulin polymerization and/or depolymerization and thus will be useful in treating diseases characterized by abnormal cell mitosis. However, these substitutions at position 2 of the estradiol rings are believed to prevent or inhibit O-dealkylation of the compositions thereby prolonging the pharmacological activity of the compositions.

Examples of compositions of the present invention include, but are not limited to:

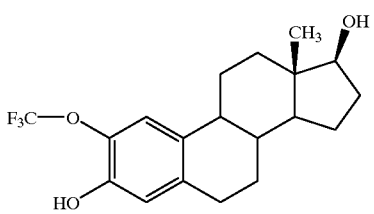

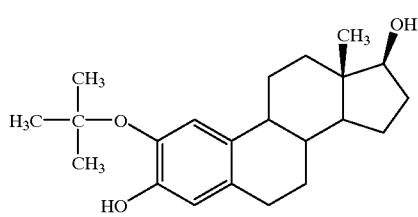

dimethyl derivative of 2-ethoxyestradiol; and

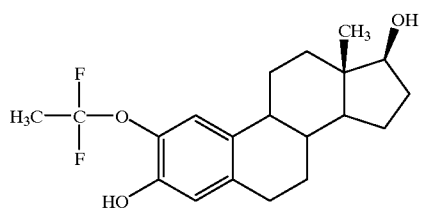

difluoro derivative of 2-ethoxyestradiol.

Compositions of the present invention can be administered via similar routes and dosing regimes to 2-methoxyestradiol. Suitable routes of administration include oral administration such as in the form of capsules, tablets, granules, and suspensions, rectal administration such as in the form of suppositories, the parenteral route, such as by injection or infusion, or the topical route such as in the form of creams, lotions or transdermal delivery systems.

Any pharmaceutically acceptable vehicle or carrier, as well as adjuvant, can be used in the manufacture, dissolution and administration of pharmaceutical preparations comprising a composition of formula (I). Such vehicles, carriers and adjuvants are well known to those of skill in the art and described in text books such as *Remington's Pharmaceutical Sciences*, Mack Publishing Co., Easton, Pa., 1985. Appropriate concentrations of active composition to be incorporated into pharmaceutical compositions can be routinely determined by those skilled in the art and is dependent upon the form of administration as well as the severity of the condition being treated.

What is claimed is:

1. A composition comprising formula (I):

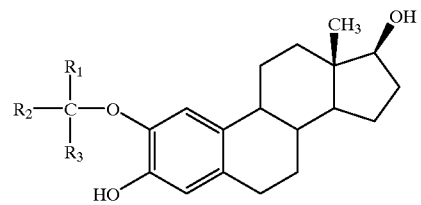

wherein $R_1$ comprises a halogen, a methyl or an alkyl group consisting of more than one carbon atom or an aromatic group, or a trifluoromethyl group; $R_2$ comprises a halogen, a methyl or an alkyl group consisting of more than one carbon atom or an aromatic group, or a trifluoromethyl group; and $R_3$ comprises a halogen, a methyl or an alkyl group consisting of more than one carbon atom or an aromatic group or a trifluoromethyl group.

2. A pharmaceutical composition comprising the composition of claim 1 and a pharmaceutically acceptable vehicle.

3. A method of inhibiting microtubule formation and tubulin polymerization or depolymerization in cells comprising administering to the cells a composition of claim 1.

4. A method for treating diseases characterized by abnormal cell mitosis comprising administering to a patient suffering from a disease characterized by abnormal cell mitosis a pharmaceutical composition of claim 2.

5. The method of claim 4 wherein the disease is cancer.

* * * * *